US012096805B2

(12) United States Patent
Guo

(10) Patent No.: US 12,096,805 B2
(45) Date of Patent: Sep. 24, 2024

(54) CHEST BINDER

(71) Applicant: DCA Commercial LTD, Denver, CO (US)

(72) Inventor: Yue Guo, Beijing (CN)

(73) Assignee: ETCHMED LLC

( * ) Notice: Subject to any disclaimer, the term of this patent is extended or adjusted under 35 U.S.C. 154(b) by 115 days.

(21) Appl. No.: 17/949,196

(22) Filed: Sep. 20, 2022

(65) Prior Publication Data

US 2023/0088253 A1 Mar. 23, 2023

(30) Foreign Application Priority Data

Sep. 23, 2021 (CN) .......................... 202111115741.0

(51) Int. Cl.
 *A41C 1/02* (2006.01)
(52) U.S. Cl.
 CPC ...................................... *A41C 1/02* (2013.01)
(58) Field of Classification Search
 CPC ....................................................... A41C 1/02
 See application file for complete search history.

(56) References Cited

U.S. PATENT DOCUMENTS

| | | | | |
|---|---|---|---|---|
| 6,138,277 A * | 10/2000 | Gillen | .................. | A41D 13/015 2/463 |
| D641,129 S * | 7/2011 | Zarabi | ............................ | D2/703 |
| 10,321,723 B2 * | 6/2019 | Kelley | .................. | A41C 3/0057 |
| 10,799,582 B2 * | 10/2020 | Bremel | ................... | C07K 16/00 |
| D916,428 S * | 4/2021 | Dixon | ............................. | D2/706 |
| D925,167 S * | 7/2021 | Picco | .............................. | D2/706 |
| 11,241,049 B2 * | 2/2022 | Utaka | ....................... | A41C 3/00 |
| 2015/0320120 A1* | 11/2015 | Kalimian | ................. | A41B 1/08 450/95 |
| 2016/0135512 A1* | 5/2016 | Smith | ...................... | A41C 5/00 450/156 |
| 2016/0374405 A1* | 12/2016 | Washington | ............. | A41C 1/02 450/76 |
| 2017/0265528 A1* | 9/2017 | Tempesta | .............. | A41C 3/0057 |
| 2023/0088253 A1* | 3/2023 | Guo | ...................... | A41D 31/185 450/115 |

* cited by examiner

*Primary Examiner* — Gloria M Hale
(74) *Attorney, Agent, or Firm* — MATTHIAS SCHOLL P.C.; Matthias Scholl

(57) ABSTRACT

A chest binder includes a front part and a back part. The front part includes a front piece including at least one layer of elastic fabric, and a percent elongation of the elastic fabric is between 1% and 5%. The back part includes an X-shaped back piece and a tightenable piece connected to the lower end of the back piece. The back piece includes an inner layer and a surface layer attached to the inner layer to form an integrated structure. The inner layer includes a left back strap and a right back strap. The tightenable piece is connected to the left back strap and the right back strap, and two sides of the tightenable piece are connected to two sides of the front piece, respectively. The front piece includes a left front strap and a right front strap.

10 Claims, 5 Drawing Sheets

CHEST BINDER

CROSS-REFERENCE TO RELATED APPLICATIONS

Pursuant to 35 U.S.C. § 119 and the Paris Convention Treaty, this application claims foreign priority to Chinese Patent Application No. 202111115741.0 filed Sep. 23, 2021, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to a chest binder.

Chest binders are specially-designed chest compression garments.

Conventionally, the front part of chest binders is not elastic resulting in chest tightness, discomfort and pain when breathing. Long-term wearing of chest binders may harm the body. Back, abdomen, and shoulder pain may occur, muscle may atrophy, posture may change, and bone deformation and fracture may result. In addition, excessive exerting of pressure on the chest will compress the breast tissue, the lymphoid system and the blood circulation system leading to corresponding diseases and conditions.

SUMMARY

The disclosure provides a chest binder, comprising a front part and a back part. The front part comprises a front piece comprising at least one layer of elastic fabric, and a percent elongation of the elastic fabric is between 1% and 5%. The back part comprises an X-shaped back piece and a tightenable piece connected to a lower end of the back piece; the back piece comprises an inner layer and a surface layer attached to the inner layer to form an integrated structure; the inner layer comprises a left back strap and a right back strap; the tightenable piece is connected to the left back strap and the right back strap, and two sides of the tightenable piece are connected to two sides of the front piece, respectively; and the front piece comprises a left front strap and a right front strap which are respectively connected to the left back strap and the right back strap.

In a class of this embodiment, the front piece comprises an inner fabric and an outer fabric attached to the inner fabric to form an integrated structure; and a percent elongation of the inner fabric is less than that of the outer fabric.

In a class of this embodiment, the inner fabric is a composite layer comprising at least two layers of elastic fabric which are attached to each other to form an integrated structure, and a percent elongation of the composite layer is less than that of the outer fabric.

In a class of this embodiment, connecting lines of the left front strap and the left back strap, and of the right front strap and the right back strap, are disposed on the back part and correspond to trapeziuses of a wearer.

In a class of this embodiment, an outer edge line of the left front strap extends from a rear side of the trapezius of the left shoulder of the wearer through an outside of the left accessory breast to a rear position of the left armpit; and an outer edge line of the right front strap extends from a rear side of the trapezius of the right shoulder of the wearer through an outside of the right accessory breast to a rear position of the right armpit.

In a class of this embodiment, an outer edge line of the left back strap extends from a rear side of the trapezius of the left shoulder of the wearer along the left shoulder blade to a vicinity of the eighth rib behind the left armpit; and an outer edge line of the right back strap extends from a rear side of the trapezius of the right shoulder of the wearer along the right shoulder blade to a vicinity of the eighth rib behind the right armpit.

In a class of this embodiment, the lower end of the outer edge line of the left back strap and the lower end of the outer edge line of the right back strap are in the vicinity of the eighth rib of the wearer.

In a class of this embodiment, the tightenable piece comprises a top edge extending to the fifth thoracic vertebra of the wearer, a bottom edge extending to the eleventh thoracic vertebra, and two sides respectively extending to two armpits.

In a class of this embodiment, a percent elongation of the inner layer of the back piece is greater than that of the front piece.

In a class of this embodiment, one layer of the composite layer intended to contact a skin of the wearer is a single sided moisture conducting fabric.

The following advantages are associated with the chest binder of the disclosure. The front piece and the back piece of the chest binder comprise elastic fabric, and the elasticity of the back piece is greater than that of the front piece, so that the back piece can lift the breast, which can effectively overcome the defects of conventional chest binders, and avoids the vibration, sliding and sagging of the breast during movement.

Figure 1:
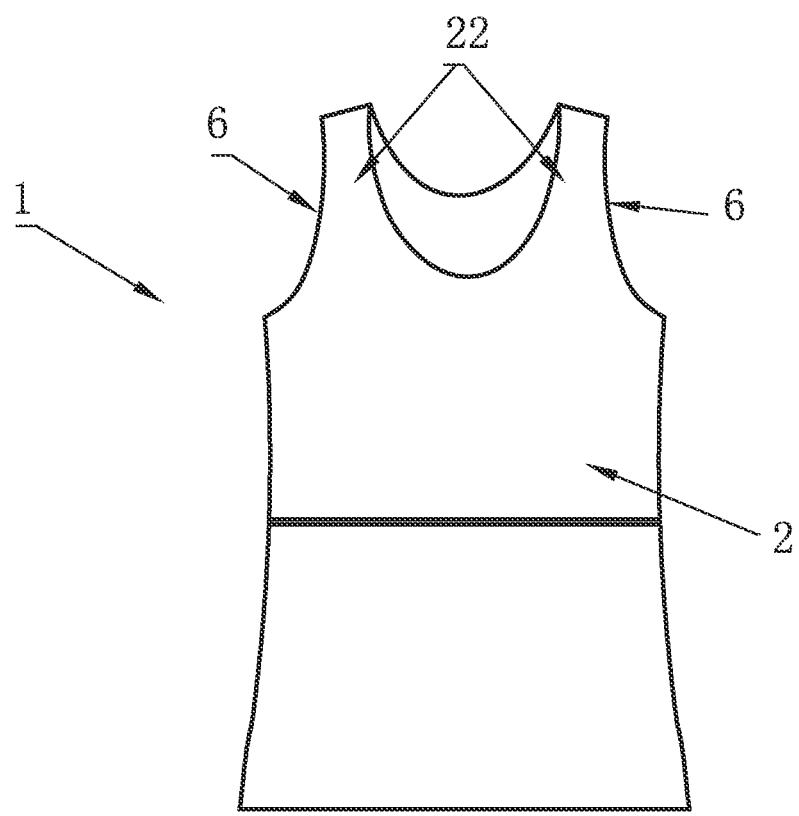
FIG. 1 is a front view of a chest binder in accordance with one embodiment of the disclosure.

In the drawings, the following reference numbers are used: 1. Chest binder; 2. Front part; 21. Front piece; 22. Front strap; 3. Back part; 31. Back piece; 32. Back strap; 4. Tightenable piece; 5. Connecting line; 6. Outer edge line.

DETAILED DESCRIPTION

To further illustrate, embodiments detailing a chest binder are described below. It should be noted that the following embodiments are intended to describe and not to limit the disclosure.

As shown in FIGS. 1-5, the disclosure provides a chest binder comprising a front part 2 and a back part 3. The chest binder is just like a T-shirt with a vest shape. The front part 2 comprises a front piece 21 and a front strap 22. The back part 3 comprises a back piece 31 and a back strap 32. The front piece 21 covers the front chest and abdomen of a wearer, the back piece 31 covers the back and waist, and the front strap 22 and the back strap 32 are connected to each other to form a collar surrounding the neck of the wearer.

1. Front Part 2

Figure 3:
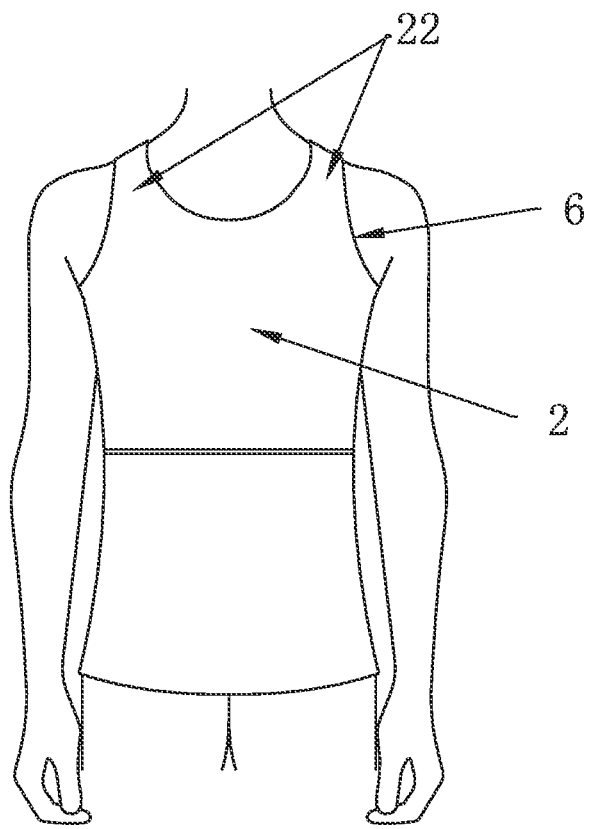
FIG. 3 is a front view of a chest binder in accordance with one embodiment of the disclosure in a use state.
Figure 5:
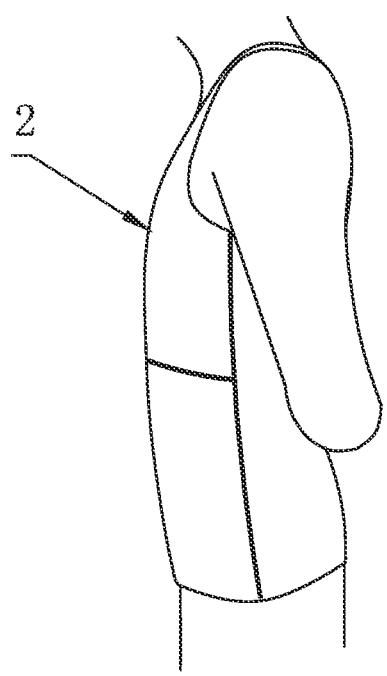
FIG. 5 is a side view of a chest binder in accordance with one embodiment of the disclosure in a use state.

As shown in FIGS. 1, 3, and 5, the front piece 21 is an integrated structure formed by hot pressing or pasting one, two or more layers of fabrics. No matter how many layers the front piece has, the percent elongation of the front piece 21 is 1%-5%. When the front piece 21 comprises multiple layers of fabrics, the percent elongation of the inner fabric is less than that of the outer fabric.

When the front piece 21 comprises one layer of fabric, it is light, air permeable, and has an integral appearance.

When the front piece 21 comprises multiple layers of fabrics, the pressure exerting on the chest is even, and has an integral appearance.

As an improvement, the inner fabric comprises at least two layers of fabrics with micro elasticity which are bonded into a composite layer with an integrated structure through hot pressing or pasting process. The total percent elongation of the composite layer is less than that of the outer fabric. The design further improves the comfort and wearing feeling.

As an improvement, one layer of the composite layer intended to contact the skin of the wearer is a single sided moisture conducting fabric that is breathable and does not stick to the body. The single sided moisture conducting fabric is characterized by being friendly to the skin and keeping the skin dry. The single sided moisture conducting fabric can quickly guide the sweat on the skin surface to the other side of the fabric away from the skin.

The chest binder 1 of the disclosure can flatten the chest and breast, and people will not feel shortness of breath during breathing. The reason is that the percent elongation is basically equal to people's chest expansion rate during normal inhalation (the chest expansion rates of different people are different, about 1%-5%). Thus, the chest binder of the disclosure can be worn for a long time comfortably.

The front part 2 and the back part 3 of the chest binder 1 form a closed-loop structure at the chest position. In general, the chest binder 1 will exert pressure on the chest. During breathing, the front part 2 will exert a pulling force on the back part 3 due to the expansion of the chest. However, because the pulling force is not enough to overcome the friction between the back part 3 and the skin, the back part 3 will not displace in the chest circumference direction. In this way, if the fabric elasticities of the front part 2 and the back part 3 are the same, the front part 2 is bound to exert great pressure on the chest. Based on this, the front part 2 of the disclosure is elastic (with a certain elongation) in order to better adapt to the change of the chest circumference when the wearer is breathing.

Expansion rate: assuming that a person's chest circumference is 100 cm, the chest circumference will increase and become larger when breathing deeply, and the expansion range is 101 cm-105 cm (varies from person to person).

Percent elongation: the change rate of the fabric circumference size of the front part 2 wrapped on the chest with the expansion of the chest.

Understandably, it is not that the higher the percent elongation, the better. If the percent elongation is too high, the pressure on the chest becomes smaller, resulting in worse binding effect. Therefore, the binding effect of the chest binder 1 of the disclosure is balanced between normal breathing and comfort.

The front piece 21 and the front strap 22 comprise the same material.

The front strap 22 comprises a left front strap and a right front strap; the back strap 32 comprises a left back strap, a right back strap, a left back brace, and a right back brace.

The left front strap and the right front strap are respectively connected to the left back strap and the right back strap. The connecting lines 5 of the left front strap and the left back strap, and of the right front strap and the right back strap, are disposed on the back part and correspond to trapeziuses of the wearer. In this way, the lifting force of the front and back straps on the chest is improved, thus preventing the shaking, sliding and sagging of the chest during movement.

The outer edge line 6 (the direction back against the body is the outside, otherwise the inside, the same below) of the left front strap extends from the rear side of the trapezius of the left shoulder of the wearer through the outside of the left accessory breast to the rear position of the left armpit; and the outer edge line 6 of the right front strap extends from the rear side of the trapezius of the right shoulder of the wearer through an outside of the right accessory breast to the rear position of the right armpit.

The chest binder of the disclosure has been redesigned and optimized in the shoulder, armpit, auxiliary breast, breast and other positions. By setting fabrics with large percent elongation locally, the compression of the chest binder 1 on soft tissue is reduced to the greatest extent, thus reducing the risk of disease.

2. Back Part 3

Figure 2:
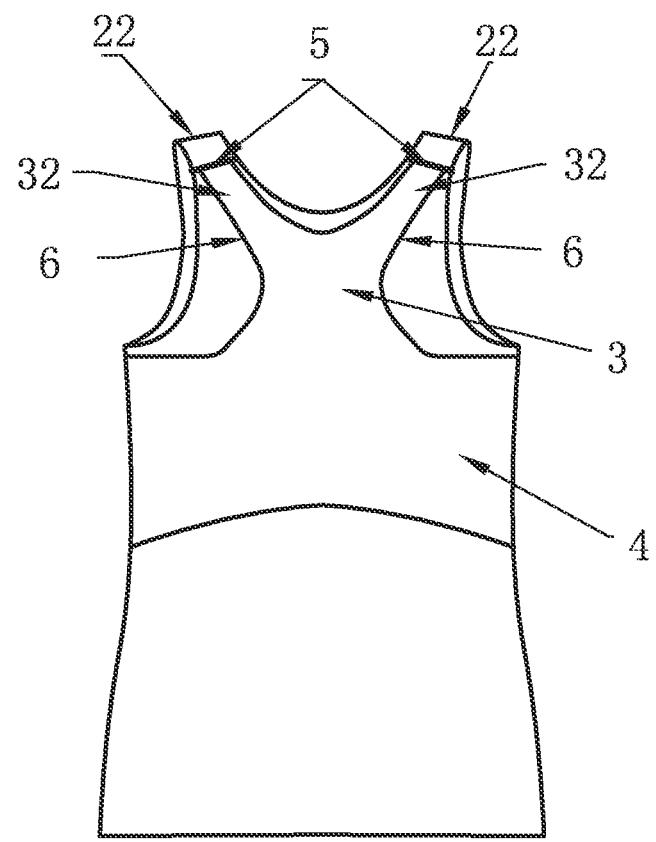
FIG. 2 is a back view of a chest binder in accordance with one embodiment of the disclosure.
Figure 4:
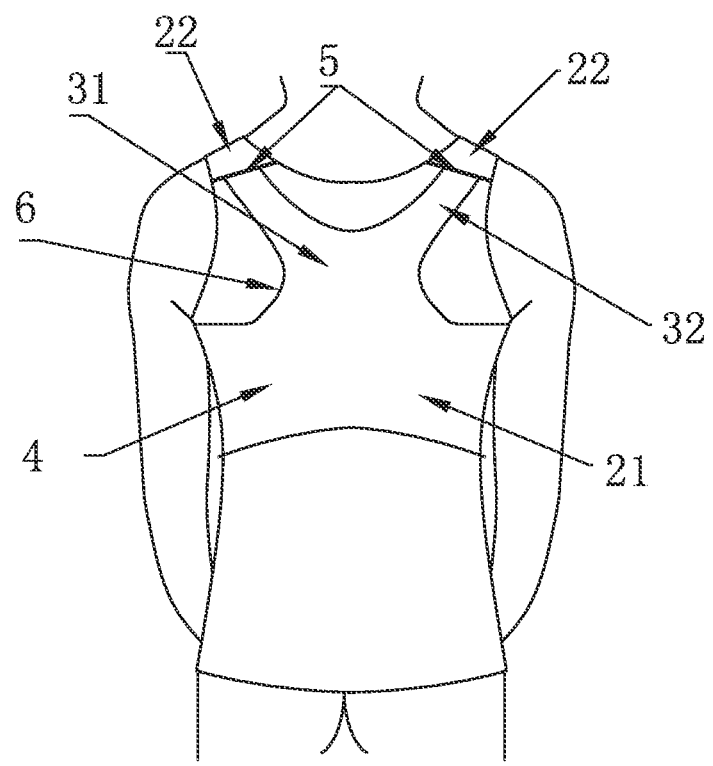
FIG. 4 is a back view of a chest binder in accordance with one embodiment of the disclosure in a use state.

As shown in FIGS. 2, 4 and 5, the back piece 31 is X-shaped and comprises an inner layer and a surface layer attached to the inner layer to form an integrated structure through a hot pressing or pasting process. The inner layer is the back strap 32, which comprises a left back strap, a right back strap, a left back brace, and a right back brace. The left back strap and the left back brace form the left half of the X-shaped structure (left strap), and the right back strap and the right back brace form the right half of the X-shaped structure (right strap).

The X-shaped structure of the inner layer is helpful to balancing the pressure exerting on the chest and back by the chest binder 1. In general, the balance of human posture comes from the balance of muscle strength. When the human body is in a normal static posture, the muscle groups of the chest and back just reach the balance of muscle strength. However, after the chest binder 1 is put on, the pressure on the chest is greater than that on the back. To balance the pressure on the chest and back, the human body has an adaptive process, which is controlled by the brain. Specifically, to maintain balance, people's back major muscles (including cervical splinter muscle, levator scapulae muscle, superior posterior saw muscle, small rhomboid muscle, supraspinatus muscle, infraspinatus muscle, teres major, latissimus dorsi, etc.) will consciously contract. For a long time, the back major muscles will be in a state of tension, resulting in back, abdominal and shoulder pain, even muscle atrophy and posture change. More seriously, this will cause bone deformation and fracture. In this disclosure, the inner layer of the back piece 31 is X-shaped and contacts and presses the back major muscle group, which can effectively improve the pressure on the back major muscle group, so as to achieve the natural balance of the muscle strength of the chest and back when people are wearing the chest binder 1 of the disclosure. Besides pressing the chest, the chest binder 1 improves the fixation effect of the breast, and effectively avoids the vibration, sliding and sagging of the breast during movement.

As an improvement, the back part 3 further comprises a tightenable piece 4 connected to the lower end of the X-shaped inner layer, preferably, in the shape of rectangle. Two sides of the tightenable piece 4 are connected to two sides of the front piece 21, respectively. The design has the following advantages: first, the pressurization area of the back is improved; second, the front piece 21 is further tightened; third, the tightenable piece 4 and the front piece 21 form a closed ring structure thus increasing the pressure on the chest.

The tightenable piece 4 comprises a top edge extending to the fifth thoracic vertebra of the wearer, a bottom edge extending to the eleventh thoracic vertebra, and two sides respectively extending to two armpits.

The outer edge line 6 of the left back strap extends from the rear side of the trapezius of the left shoulder of the wearer along the left shoulder blade to the vicinity of the eighth rib behind the left armpit; and the outer edge line 6 of the right back strap extends from the rear side of the trapezius of the right shoulder of the wearer along the right shoulder blade to the vicinity of the eighth rib behind the right armpit.

The lower end of the outer edge line 6 of the left back strap and the lower end of the outer edge line 6 of the right back strap are in the vicinity of the eighth rib of the wearer.

The advantage of the above structure is that the lower edge of the front part 2 is not lower than the eighth rib. On the one hand, the breast is just completely covered, on the other hand, no excessive pressure is imposed on the abdominal cavity (unlike the chest cavity protected by ribs, the abdominal cavity is a hollow organ).

It will be obvious to those skilled in the art that changes and modifications may be made, and therefore, the aim in the appended claims is to cover all such changes and modifications.

What is claimed is:

1. A chest binder, comprising:
   a front part; and
   a back part;
   wherein:
   the front part comprises a front piece comprising at least one layer of elastic fabric, and a percent elongation of the elastic fabric is between 1% and 5%;
   the back part comprises an X-shaped back piece and a tightenable piece connected to a lower end of the back piece; the back piece comprises an inner layer and a surface layer; the surface layer is attached to the inner layer to form an integrated structure; the inner layer comprises a left back strap and a right back strap;
   the tightenable piece is connected to the left back strap and the right back strap, and two sides of the tightenable piece are connected to two sides of the front piece, respectively; and
   the front piece comprises a left front strap and a right front strap which are respectively connected to the left back strap and the right back strap.

2. The binder of claim 1, wherein the front piece comprises an inner fabric and an outer fabric attached to the inner fabric to form an integrated structure; and a percent elongation of the inner fabric is less than that of the outer fabric.

3. The binder of claim 2, wherein the inner fabric is a composite layer comprising at least two layers of elastic fabric which are attached to each other to form an integrated structure, and a percent elongation of the composite layer is less than that of the outer fabric.

4. The binder of claim 3, wherein connecting lines of the left front strap and the left back strap, and of the right front strap and the right back strap, are disposed on the back part and are configured to correspond to trapeziuses of a wearer.

5. The binder of claim 4, wherein an outer edge line of the left front strap is configured to extend from a rear side of a trapezius of a left shoulder of the wearer through an outside of a left accessory breast of the wearer to a rear position of a left armpit of the wearer; and an outer edge line of the right front strap is configured to extend from a rear side of a trapezius of a right shoulder of the wearer through an outside of a right accessory breast of the wearer to a rear position of a right armpit of the wearer.

6. The binder of claim 5, wherein an outer edge line of the left back strap is configured to extend from the rear side of the trapezius of the left shoulder of the wearer along a left shoulder blade of the wearer to a vicinity of an eighth rib behind the left armpit of the wearer; and an outer edge line of the right back strap is configured to extend from the rear side of the trapezius of the right shoulder of the wearer along a right shoulder blade of the wearer to a vicinity of an eighth rib behind the right armpit of the wearer.

7. The binder of claim 6, wherein a lower end of the outer edge line of the left back strap and a lower end of the outer edge line of the right back strap are configured to be in the vicinity of the eighth rib behind the left armpit of the wearer and the eighth rib behind the right armpit of the wearer, respectively.

8. The binder of claim 7, wherein the tightenable piece comprises a top edge configured to extend to a fifth thoracic vertebra of the wearer, a bottom edge configured to extend to an eleventh thoracic vertebra of the wearer, and two sides configured to respectively extend to the left armpit and the right armpit of the wearer.

9. The binder of claim 8, wherein a percent elongation of the inner layer of the back piece is greater than that of the front piece.

10. The binder of claim 8, wherein one layer of the composite layer intended to contact skin of the wearer is a single sided moisture conducting fabric.

* * * * *